(12) United States Patent
Bhaskaran

(10) Patent No.: US 8,883,461 B2
(45) Date of Patent: Nov. 11, 2014

(54) **PROCESS FOR THE PRODUCTION OF VIOLACEIN AND ITS DERIVATIVE DEOXYVIOLACEIN CONTAINING BIOACTIVE PIGMENT FROM *CHROMOBACTERIUM* SP. (MTCC5522)**

(75) Inventor: Krishnakumar Bhaskaran, Kerala (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/634,329

(22) PCT Filed: Mar. 10, 2011

(86) PCT No.: PCT/IB2011/000507
§ 371 (c)(1),
(2), (4) Date: Nov. 26, 2012

(87) PCT Pub. No.: WO2011/110932
PCT Pub. Date: Sep. 15, 2011

(65) Prior Publication Data
US 2013/0074735 A1    Mar. 28, 2013

(30) Foreign Application Priority Data
Mar. 12, 2010    (IN) .............................. 577/DEL/2010

(51) Int. Cl.
C12P 17/16    (2006.01)
C12R 1/01    (2006.01)
C12N 1/20    (2006.01)
C09B 61/00    (2006.01)

(52) U.S. Cl.
CPC ... *C12N 1/20* (2013.01); *C12R 1/01* (2013.01); *C09B 61/00* (2013.01); *C12P 17/165* (2013.01)
USPC ........................................................ 435/118

(58) Field of Classification Search
None
See application file for complete search history.

(56) References Cited

U.S. PATENT DOCUMENTS

| 4,529,698 A | 7/1985 | Sykes et al. |
| 4,859,593 A | 8/1989 | Umezawa et al. |
| 5,356,794 A | 10/1994 | Fromageot et al. |

(Continued)

FOREIGN PATENT DOCUMENTS

| CN | 101319219 | 12/2008 |
| CN | 101368169 | 2/2009 |

(Continued)

OTHER PUBLICATIONS

"*Chromobacterium* sp. keralian 16S ribosomal RNA gene, partial sequence", retrieved from EBI accession No. EM-PRO:FJ982784, dated Jun. 7, 2009.*

(Continued)

*Primary Examiner* — Patricia A Leith
*Assistant Examiner* — Erin M Bowers
(74) *Attorney, Agent, or Firm* — Hamre, Schumann, Mueller & Larson, P.C.

(57) ABSTRACT

The present invention discloses a process for producing purple-blue natural pigment containing violacein and its derivative (deoxyviolacein) using *Chromobacterium* sp. NIIST-CKK-01 (MTCC 5522, NCIM 5341; Genbank Accession No. FJ982784). The method comprises the steps of maintaining and growing the bacterium in a specific medium under defined conditions of pH, temperature and agitation. At the end of incubation, pigment and biomass is separated from the culture broth, pigment is recovered from the biomass through solvent extraction and finally pigment is concentrated by drying.

6 Claims, 5 Drawing Sheets

(56) References Cited

U.S. PATENT DOCUMENTS

| | | |
|---|---|---|
| 5,428,175 A | 6/1995 | Hoshino et al. |
| 7,244,607 B2 | 7/2007 | Martin et al. |
| 2004/0053375 A1 | 3/2004 | Tan et al. |
| 2006/0263368 A1 | 11/2006 | Rosenblum et al. |

FOREIGN PATENT DOCUMENTS

| | | |
|---|---|---|
| CN | 101386834 | 3/2009 |
| DE | 3813465 | 11/1989 |
| DE | 3935066 | 4/1991 |
| DE | 10063712 | 8/2002 |
| DE | 102005051869 | 4/2007 |
| EP | 1341925 | 8/2007 |
| JP | 6253864 | 9/1994 |
| JP | 6341069 | 12/1994 |
| JP | 7227290 | 8/1995 |
| JP | 10113169 | 5/1998 |
| JP | 10139612 | 5/1998 |
| JP | 11152687 | 6/1999 |
| KR | 20070088150 | 8/2007 |
| WO | 99/20799 | 4/1999 |
| WO | 02/50299 | 6/2002 |
| WO | 2004/056960 | 7/2004 |
| WO | 2005/032250 | 4/2005 |
| WO | 2006/074451 | 7/2006 |

OTHER PUBLICATIONS

Mendes et al., Biotech. Lett. 23: 1963-1969 (2001).*

D. Rettori and N. Duran, "Production, extraction and purification of violacein: an antibiotic pigment produced by *Chromobacterium violaceum*", World Journal of Microbiology and Biotechnology, vol. 14, Jan. 1, 1998, pp. 685-688.

R.Riveros, M. Haun and N. Duran, "Effect of Growth Conditions on Production of Violacein by *Chromobacterium violaceum*", Brazilian Journal of Medical and Biological Research, vol. 22, No. 5, 1989, pp. 569-577.

R. D. Demoss and N.R. Evans, "Physiological Aspects of Violacein Biosynthesis in Nonproliferating Cells", J Bacteriol, Oct. 1959, p. 583-588.

R. Sivendra and H.S.Lo, "Identification of *Chromobacterium violaceum*: Pigment and Non-pigment Strains", Journal of General Microbiology 90 (1), Sep. 1975, p. 21-31.

J.A. Demoss, Robert W. Jackwon and John H. Chalmers, "Genetic Control of the Structure and Activity of an Enzyme Aggregate in the Tryptophan Pathway of *Neurospora crassa*", Genetics 56 (3), Jul. 1967, pp. 413-424.

International Search Report for international application PCT/IB2011/000507, dated Jul. 20, 2011 (4 pages).

Written Opinion for international application PCT/IB2011/000507, dated Jul. 20, 2011 (7 pages).

"*Chromobacterium* sp. Keralian 16S ribosomal RNA gene, partial sequence," retrieved from EBI accession No. EM-PRO:FJ982784, dated Jun. 7, 2009 (1 page).

* cited by examiner

PROCESS FOR THE PRODUCTION OF VIOLACEIN AND ITS DERIVATIVE DEOXYVIOLACEIN CONTAINING BIOACTIVE PIGMENT FROM *CHROMOBACTERIUM* SP. (MTCC5522)

FIELD OF THE INVENTION

The present invention relates to an isolated bacterial strain, *Chromobacterium* sp. having accession no. MTCC 5522 deposited on 27 Jan. 2010. Also, the present invention provides a process for the production of violacein and its derivatives containing natural bioactive pigment using a new bacterial isolate *Chromobacterium* sp. NIIST-CKK-01 (MTCC 5522, NCIM no. 5341; Genbank accession no. FJ982784). More particularly, invention relates to a method for the production of a bioactive pigment containing violacein and its derivatives using *Chromobacterium* sp. NIIST-CKK-01 maintained and grown in specific medium under defined conditions and subsequent recovery of the pigment from the culture medium.

BACKGROUND OF THE INVENTION

Microbial secondary metabolites have a major effect on health, nutrition and economics of human society. These secondary metabolites include antibiotics, antiviral, cytotoxins, pigments, antioxidants, pheromones, enzyme inhibitors, immunomodulators, antitumour agents and growth promoters exhibiting a spectrum of biological activity. "Violacein" (3-[1,2-dihydro-5-(5-hydroxy-1H-indol-3-yl)-2-oxo-3H-pyrrol-3-ylidene]-1,3-dihydro-2H-indol-2-one) is a purple-blue coloured indole derivative and secondary metabolite, isolated mainly from bacteria of the genus *Chromobacterium*. Violacein exhibits important biological activities that have important pharmaceutical applications including antitumoural, anti-bacterial, antiviral, enzyme modulation, cytotoxic, antiprotozoa and protects from ionizing radiations and antiparasitary properties (Dural et al., 2007).

The biological role of violacein in *Chromobacterium violaceum*, as well as its biosynthesis pathway is studied intensively. Violacein is found to be a respiratory pigment (Friedheim, 1936) and its production is involved in the regulation of tryptophan synthesis (DeMoss, 1967). L-tryptophan is readily converted to violacein by *Chromobacterium violaceum*. However, violacein is not required for growth and survival of *C. violaceum* since pigment production stops when *C. violaceum* is grown on complex and complete medium (Sivendra and Lo, 1975; Durán and Faljoni-Alario, 1980). Although *C. violaceum* is able to grow under both aerobic and anaerobic conditions, violacein production occurs only in the presence of oxygen (DeMoss and Evans, 1959). When the enzymes of the violacein pathway are inactivated by rapid lyophilization, both *L. tryptophan* and indole were metabolized to indigo, another purple pigment used as dye (O. Sebek, and H. Jaeger, Nature, 1962, 196, 793-795). Pub No. WO/2004/056960 discloses the genes encoding polynucleotides of the chromosome of *Chromobacterium violaceum*, expression activity and applications of these polynucleotides. In addition to producing violacein, a species of *Chromobacterium*, *Chromobacterium suttsuga* sp. *nov* was found to exhibit insecticidal activity as revealed in Pub No. WO/2005/032250. *Chromobacterium violaceum* also produces other useful compounds such as physiologically active compound HS-1 having antitumor and antimicrobial activity (U.S. Pat. No. 5,428,175), a purified enzymatic preparation used for production of alpha, beta-dehydrotyrptophanyl peptides (U.S. Pat. No. 5,356,794), arphamenine which is useful as a host defence stimulator, anti-tumor agent and to enhance cell-mediated immunity (U.S. Pat. No. 4,859,593), and 2-oxo-1-azetidinesulfonic acid salt having antibiotic activity (U.S. Pat. No. 4,529,698).

The purple pigment produced by *Chromobacterium violaceum* is a composite of violacein (about 90%) and other compounds such as deoxy violacein (DeMoss and Evans (1959) a less abundant pigment, trans-hydroxy violacein or its derivatives, triacetylviolacein and diacetyl(di)methylviolacein.

References may be made to patent "BR200101346A" wherein process for application of violacein as an anti-microbiotic, using the active agent dissolved in dimethylsulfoxide for subsequent use in aqueous solutions is disclosed.

References may be made to patent "WO/2006/074451 (US 20060263368)" wherein inventor discloses the use of violacein as a cytotoxic agent or anti-cell proliferation moiety for cancer therapy. For combating tumors and to enhance toxicity reduction capacity, a formulation of violacein encapsulated in hydrophobic compound such as beta-cyclodextrin conjugated with a gold nanoparticle via a specific dithiol and the process using the encapsulated violacein are claimed in Patent No BR200502657. References may be made to patent "KR2007088150" wherein inventors discloses a pest controlling agent comprising violacein derived from *Chromobacterium violaceum* having pest-controlling as well as anti-fungal activity and method for preparing violacein.

A cosmetic preparation useful as antibacterial and antiviral for protection of skin and mucous membrane and comprising violacein dye, trans-hydroxy violacein, desoxyviolacein, deoxyviolacein or its derivatives, triacetylviolacein and diacetyl(di)methylviolacein and or its furan analogs, in combination with lipophilic and/or hydrophilic substances is disclosed in Patent No. DE102005051869. A process for preparing pure trans-hydroxyviolacein, process for preparing its use for the prophylaxis and therapy of viral diseases is disclosed in Patent No. DE 3813465.

The bluish violet pigment such as violacein or deoxyviolacein produced from *Janthinobacterium lividum* is treated with an aqueous solution of thiourea for improving light resistance of the pigment as disclosed in Patent No. JP11152687. Patent No BR9801307 discloses a formulation of cyclodextrin/violacein with enhanced violacein solubility and versatility for use in medicine as an anti-tumour, antibacterial, antiviral and trypanocidal agent. Antiparasitic, antifungal agent containing violacein is disclosed in the patent KR20070088150. Violacein from *Pseudoalteromonas* sp. of "black beauty" strain (DSM 13623) for application in food, textile and toy industry was reported in patent no US 2004053375.

A procedure for the production, extraction, and purification of violacein was developed by D. Rettori and N. Duran (World J. Microbiol. Biotech. 1998, 14, 685-688), using *Chromobacterium violaceum* (CCT 3496) cultivated on cotton, in modified 1 liter Roux bottles. Patent No BR9702918-A discloses a process for biosynthesis of violacein having anti tumour activity, using rice as carbon source in agar nutrient medium. Violacein having antiviral activity against polio and herpes viruses can be prepared by cultivating *Chromobacterium violaceum* in an aerated batch fermenter at 20-25° C. for 5-7 days in a medium containing peptone, glucose and common salt at a pH of 6-7, extracting the crude pigment using ethanol and then re-extracting using n-heptane, as disclosed in Patent No DE3935066.

The yield of violacein from *Chromobacterium violaceum* using known microbiological methods is very low (0.43 g/L)

for large scale commercial applications. Japanese Patent No. JP 7227290 discloses an inexpensive industrial method of adding a tryptophan source, anthranilic acid or its salt in a given concentration to the liquid culture of *Chromobacterium* sp and extracting violacein from the cell or liquid medium or both. Use of surface shelves type bioreactor for bacterial metabolite (violacein) production, extraction and purification is disclosed in Patent No. BR9702986. A natural antimicrobial antioxidant from *Chromobacterium* and *Janthinobacterium* and their cosmetic preparation is disclosed in Pat no. JP 10139612. Patent No. JP6253864 discloses a method for preparing violacein by inoculating either or both *Chromobacterium* and *Janthinobactrium* in broth.

To meet the demand for violacein, it is extracted economically using simple technical processes from other species also. A marine sediment bacterium *Pseudoalteromonas* sp strain Black Beauty (originally deposited under file number DSM 13623) gave thirteen-fold yield and the crude dye was extracted from the cell mass by slurrying with hot methanol as disclosed in Patent No. AT000000369438, DE000010063712, EP000001341925, US020040053375, WO002002050299. *Janthinobacterium lividum* S9601 strain (deposited as FERM P-15894), isolated from refuse cocoons or stained silk yarns also produces a derivative of violacein, which is used as a dye with excellent color tone, fabric hand and fastness of dyeing (JP 10113169). A protease and violacein are simultaneously produced using a liquid culture of *Chromobacterium* and *Janthinobacterium* sp containing decomposed matter of animal hair and dipping protein fiber product of animal hair or silk effectively improves a feeling of fibers and carries out dying at the same time (JP 6341069).

Recombinant strains of bacteria have been employed for producing violacein pigment and their derivatives. A method for producing special recombination strains of bacteria by introducing deoxyviolacein synthesis related gene clusters and producing deoxyviolacein is disclosed for *Pseudomonas putida* in Patent No. CN 101386834 and Patent No. CN 101368169 and for *Bacillus coli* BL21-CodonPlus (DE3)-RIL in Patent No. CN 101319219, for *E. coli* in Pub No. WO/1999/020799.

U.S. Pat. No. 7,244,607 discloses *Chromobacterium subtsugae* sp. nov. that produces purple coloured metabolites having insecticidal activity. Compared to *Chromobacterium subtsugae* sp. nov., *Chromobacterium* sp. NIIST-CKK-01 in the present invention produces the pigment at a short incubation period with simple nutritional requirements. The present invention overcomes the draw back of low yield of violacein pigment production, using a new strain of *Chromobacterium*, named *Chromobacterium* sp. NIIST-CKK-01 (NCIM 5341) maintained and grown in specific culture media under defined growth conditions and extracting the violacein pigment using an organic solvent such as methanol, ethanol or butanol. The main advantage of this invention is the enhanced production of the violacein containing bioactive pigment in comparatively less time and the pigment produced is stable even at high temperatures and over wide pH range.

OBJECTIVE OF THE INVENTION

The main objective of the present invention is to provide an isolated bacterial strain, *Chromobacterium* sp. having accession no. MTCC 5522

Another objective of the present invention is to provide a process for enhanced production of violacein and its derivatives containing natural bioactive pigment using *Chromobacterium* sp. NIIST-CKK-01 (NCIM 5341; Genbank accession no. FJ982784), maintained and grown in specific culture media under defined growth conditions.

Yet another objective of the present invention is separation and purification of violacein and its derivatives containing natural bioactive pigment from *Chromobacterium* sp. NIIST-CKK-01 (MTCC 5522, NCIM 5341; Genbank Accession No. FJ982784), maintained and grown in specific culture media under defined growth conditions.

SUMMARY OF THE INVENTION

Accordingly, present invention provides an isolated bacterial strain, *Chromobacterium* sp. having accession no. MTCC 5522, wherein the said *Chromobacterium* cells are 0.3 to 0.6 inn wide and 0.9 to 1.5 μm long, facultative aerobic Gram negative, Oxidase positive, Indole production test negative, Methyl red test positive, Voges-Proskauer test negative, Citrate utilization test positive, TSI test glucose fermenting only, Catalase test negative and Ureas test negative. Further, present invention provides a process for the production of microbial purple-blue bioactive pigment containing violacein and its derivative deoxyviolacein using a new bacterial isolate *Chromobacterium* sp. deposited at MTCC, IMTECH, Sector 39A, Chandigarh 160036 India, and having accession no. MTCC 5522, wherein the said process comprising the steps of:

a) inoculating *Chromobacterium* sp. having accession no. MTCC 5522 in a growth medium at pH in the range of 5 to 9 at temperature in the range of 27 to 32° C. for a period in the range of 8 to 30 hrs under stirring at 150 to 250 rpm to obtain bacterial biomass containing pigment;

b) mixing the bacterial biomass containing pigment as obtained in step (a) with a solvent in the ratio ranging between 1:3 to 1:5 to obtain a mixture;

c) optionally, centrifuging the bacterial biomass with pigment as obtained in step (a) at the speed in the range of 9660×g to 10,000×g at a temperature ranging between 4 to 7° C. for period in the range of 10 to 15 minutes to obtain supernatant free cell pellet containing biomass and pigment;

d) mixing the cell pellet containing biomass and pigment as obtained in step (c) with a solvent in the ratio ranging between 1:3 to 1:5 to obtain a mixture;

e) centrifuging the mixture as obtained in step (d) or in step (b) at the speed in the range of 9660×g to 10,000×g at a temperature ranging between 4° C. and 7° C. for period in the range of 10 to 15 minutes to obtain solvent extracted pigment;

f) concentrating solvent extracted pigment as obtained in step (e) by rotor evaporation or vacuum drying at temperature ranging between 50° C. to 70° C. to obtain microbial purple-blue bioactive pigment containing violacein and its derivative deoxyviolacein.

In an embodiment of the present invention, pH is in the range of 6.5 to 7.5 and time period is in the range of 20 to 24 hrs.

In yet another embodiment of the present invention, growth medium comprises 0.4 to 0.5% Yeast extract and 1 to 1.5% Peptone or 0.5 to 1% Starch, 0.25 to 0.75% Peptone and 0.1 to 0.3% Yeast extract.

In yet another embodiment of the present invention, solvent used is selected from the group consisting of ethanol, methanol, butanol or a combination there of.

In yet another embodiment of the present invention, the yield of the said bioactive pigment is in the range of 0.6 to 1.0 g pigment/g of dry biomass after 24 hrs incubation period.

In yet another embodiment of the present invention, the said bioactive pigment inhibits the growth of 93-97% gram positive bacteria, 55-60% of gram negative bacteria, 10-20% of fungal growth, 20-30% of protozoa growth and exhibits free radical scavenging property.

In yet another embodiment of the present invention, the said bioactive pigment is stable at temperature in the range of 0° C. to 80° C. and at pH in the range of 2 to 8.

In yet another embodiment of the present invention, an isolated bacterial strain, *Chromobacterium* sp. having accession no. MTCC 5522, wherein the said *Chromobacterium* cells are 0.3 to 0.6 μm wide and 0.9 to 1.5 μm long, facultative aerobic Gram negative, Oxidase positive, Indole production test negative, Methyl red test positive, Voges-Proskauer test negative, Citrate utilization test positive, TSI test glucose fermenting only, Catalase test negative and Ureas test negative.

In yet another embodiment of the present invention, used *Chromobacterium* sp. is isolated from clay mine acid lake sediment from Thiruvananthapuram district in Kerala, India.

In yet another embodiment of the present invention, the pigment produced is extracted directly or after separating the biomass from the culture broth.

In yet another embodiment of the present invention, the organic solvent used for the extraction of bacterial pigment violacein is directly added to the culture broth containing the biomass and the bioactive pigment for whole broth extraction.

DETAILED DESCRIPTION OF THE INVENTION

Figure 1:
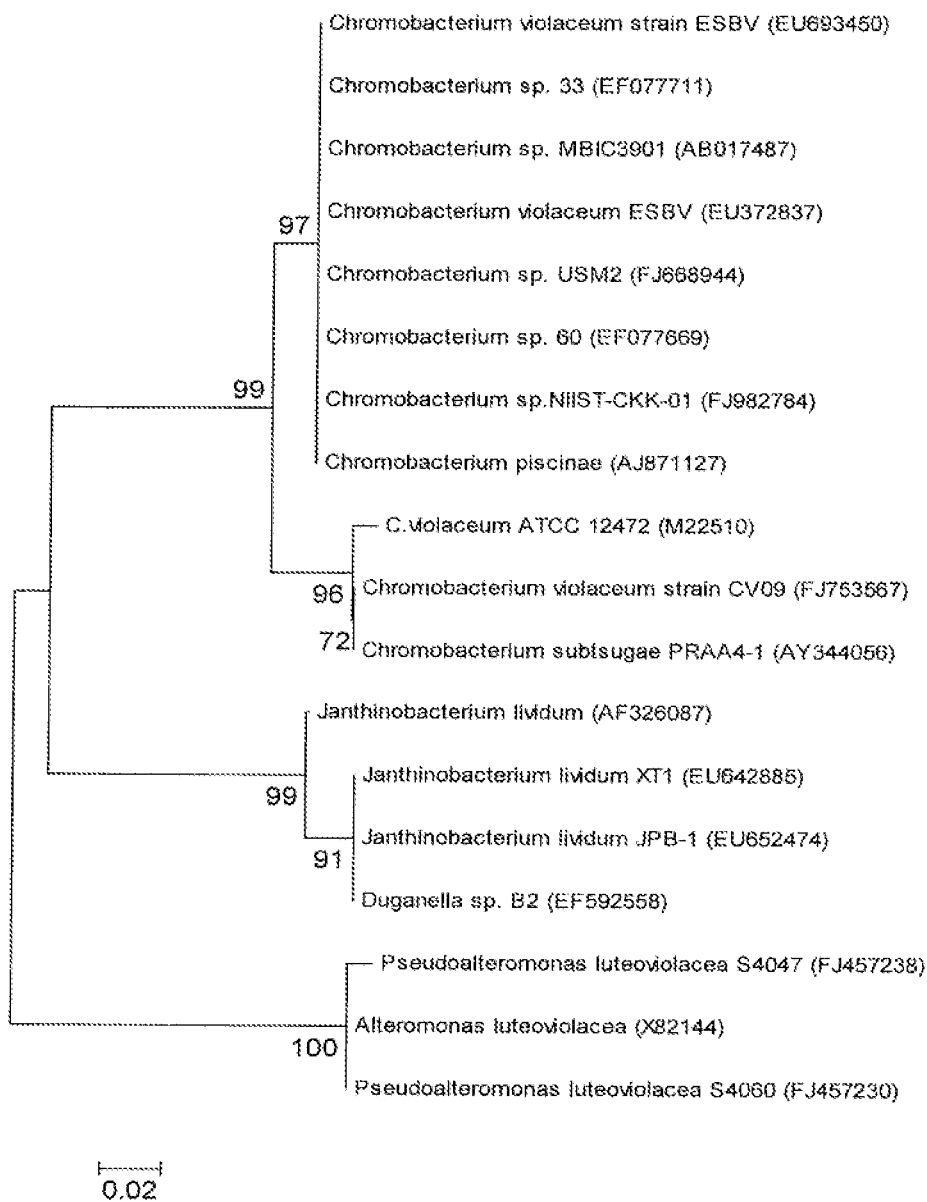
FIG. 1 represent Neighbour-joining phylogram based on 16S rRNA gene sequences showing the phylogenetic position of *Chromobacterium* sp. NIIST-CKK-01 with other violacein producing organisms retrieved from the GenBank. Scale bar represents 0.02 substitutions per nucleotide position.

The present invention discloses *Chromobacterium* sp. NIIST-CKK-01 cells, 0.3 to 0.6 μm wide and 0.9 to 1.5 μm long, facultative aerobic Gram negative, Oxidase positive, Indole production test negative, Methyl red test positive, Voges-Proskauer test negative, Citrate utilization test positive, TSI test glucose fermenting only, Catalase test negative and Ureas test negative.

Also, present invention provides a process for the production of purple-blue natural bioactive pigment containing violacein and its derivatives using a bacterium *Chromobacterium* sp. NIIST-CKK-01 (MTCC 5522, NCIM 5341; Genbank accession no. FJ982784), maintained and grown in specific culture media under defined growth conditions.

In this process, a new biologically pure isolate of *Chromobacterium* sp. NIIST-CKK-01 (culture deposited to NCIM; Genbank accession no. FJ982784) maintained and cultured in a specific culture medium by inoculating the culture media of pre-defined composition with appropriate amount of inoculum and growing under defined conditions of pH, temperature and agitation. After the incubation of culture for a specific period, the bacterial biomass was separated from culture medium through centrifugation. The recovery of substance from biomass was carried out by extraction with a suitable organic solvent added to the culture in a pre-determined ratio. The extracted pigment was then concentrated by rotor evaporation or vacuum drying at a defined temperature.

*Chromobacterium* sp. NIIST-CKK-01 is maintained in a solid medium of 0.5% Yeast extract and 1.5% Peptone and 1.5% agar, under refrigerated condition of 4-7° C. for not more than two weeks.

The main advantage of this invention is the enhanced production of violacein and its derivative containing natural pigment in short duration and the bioactive pigment produced is stable even at very high temperatures and over a wide pH range.

*Chromobacterium* sp. NIIST-CKK-01 is an aerobic bacterium, isolated from clay mine acid lake sediment from Thiruvananthapuram district in Kerala, India. The taxonomic position of the bacterium is Bacteria; Proteobacteria; Neisseriales; Neisseriaceae; *Chromobacterium*; *Chromobacterium* sp. NIIST-CKK-01. The bacterium is able to utilize organic substrates like acetate, glucose, starch, glycerol and grown in Luria Britani (LB) agar medium (composition (g/L) peptone-10, yeast extract-5, NaCl-5, agar-15) or broth, Nutrient agar medium (composition (g/L) peptone-5, beef extract-3, yeast extract-5, agar-15) or broth, R2A agar medium (composition (g/L) Casine acid hydrolysate-0.5, yeast extract-0.5, protease peptone-0.5, dextrose-0.5, soluble starch-0.5, dipotassium phosphate-0.3, $MgSO_4$-0.3, sodium puruvate-0.3, agar-15 g). Colonies of *Chromobacterium* sp. NIIST-CKK-01 are circular, deep violet in colour, and opaque with glossy surface on LB agar, Nutrient agar and R2A agar media. The colony diameter ranges from 12-20 mm. The strain is found to be gram negative. The strain tested positive for biochemical tests such as oxidase, methyl red as well as citrate utilization tests and negative for catalase, urease, indole production and Voges-proskauer tests. Triple Sugar Indole (TSI) test positive for glucose and without sulphide production. SEM (Scanning Electron Microscope) observation showed that the cell size ranges from 0.4-0.6×1.8-2.2 μm.

As used herein, all % are percent weight to weight, also expressed as % (w/w) unless otherwise specified. In this process *Chromobacterium* sp. NIIST-CKK-01 is cultured in a specific growth medium containing 0.2-0.7% Yeast extract and 1.2-1.7% Peptone on a weight per weight basis. Culture medium containing 0.5-1% Starch, 0.2-0.7% Peptone and 0.1-0.5% Yeast extract on a weight per weight basis is used.

The culture medium is inoculated with 1-5% (v/v on volume basis) of *Chromobacterium* sp. MIST-CKK-01 bacterial cell inoculum. For enhanced bioactive dye production, *Chromobacterium* sp. NIIST-CKK-01 is cultured by maintaining the pH of the culture media at 5-9, the optimum pH being 6.5-7.5, and temperature of the culture medium optimum at 30° C. and maintaining agitation of culture at 150-250 rpm. The culture is incubated for a period of 20-24 hrs.

When confluence is reached, the bacterial biomass is separated from the liquid culture medium by centrifugation and bioactive pigment is extracted from the bacterial biomass by extraction using organic solvents such as ethanol, methanol or butanol added to the initial culture broth in 1:3 ratio. The bioactive pigment thus recovered is concentrated or dried by evaporation using a rotor or by vacuum drying at temperature in the range of 50-60° C. The bioactive pigment thus produced from *Chromobacterium* sp. NIIST-CKK-01 exhibits stability at a temperature range of 20-80° C. and pH range of 5-9. The yield of microbial pigment violacein obtained is about 0.6-1.0 g per gram of culture on a dry weight basis in 24 hrs incubation period.

TABLE 1

Effect of temperature on the stability of violacein pigment from C. NIIST-CKK-01

| Temp. ° C. | Absorbance (575 nm) after 1 hr incubation at different temperatures |
|---|---|
| 0 | 1.506 |
| 4 | 1.506 |
| 30 | 1.506 |
| 40 | 1.509 |
| 60 | 1.495 |
| 80 | 1.488 |

TABLE 2

Effect of pH on the stability of violacein pigment from C. NIIST-CKK-01

| pH | Absorbance (575 nm) after 1 hr incubation at different pH |
|---|---|
| 2 | 1.467 |
| 4 | 1.420 |
| 6 | 1.482 |
| 8 | 1.468 |

*Chromobacterium* sp. NIIST-CKK-01 is an aerobic bacterium, isolated from clay mine acid lake sediment from Thiruvananthapuram district in Kerala, India. The bacterium was found associated with Kaolin type clay particles. It was initially isolated on Nutrient agar medium (composition (g/L) peptone-5, beef extract-3, yeast extract-5, agar-15).

Characterization of *Chromobacterium* sp. NIIST-CKK-01 revealed it can utilize simple and complex organic substrates for growth and produced pigment without exogenous L-tryptophan in the medium. Among the carbon sources, glucose enhanced growth, but inhibited pigment production. The pigment was produced within 5-9 pH, 20-40° C., salinity up to 1.5% and under aerobic to microaerophilic condition. At pH 4, 4.5 and 10 slight growth was observed, but no pigment production. This is the first report of a violacein producing bacterial growth under a wide pH range. For *C. violaceum* strain BB-78 maximum pigment production was observed at pH 7 (Riveros et al., 1989). The psychrotrophic strain RT 102 showed maximum cell concentration and pigment production at pH 6 (Nakamura et al., 2002). Similarly, optimum pH for violacein production by *Duganella* sp. B2 was pH 6.71 (Wang et al., 2009).

During 24 hr incubation in the specific medium (composition 0.5% yeast extract, 1.5% peptone) *Chromobacterium* sp. NIIST-CKK-01 under optimum conditions of pH 7,30° C. and under 200 RPM agitation, produced 1 g violacein/gram biomass (dry wt.) which is higher than any of previous reports.

The highest violacein production reported so far is in *Duganella* sp. B2 (1.62 g/L in 32 hrs) under optimum conditions of pH (6.72), temperature (40° C.), agitation (200 ml) in 25 ml volume of a defined media containing L-tryptaphan as the precursor for violacein biosynthesis (Wang et al., 2009). Whereas, *Chromobacterium* sp. NIIST-CKK-01 is better in terms of simple nutrient requirement, growth conditions, early pigment production and pigment yield. The pigment production was declined by the presence of glucose, however total inhibition was not observed.

Temperature considerably affected pigment production by *Chromobacterium* sp. NIIST-CKK-01, but showed little effect on growth in the present strain. At 30° C., violacein production started in 10 hours incubation, whereas at 35° C. pigment production started around 6 hours. The maximum pigment production was found at 30° C. in 24 hours incubation period.

The present strain exhibited maximum growth in media free of salinity, but around 55% decline in growth was observed at 1.5% salinity. On the other hand, pigment production at 1.5% salinity was 10% lower compared to salinity free media.

Phylogenetic analysis based on 16S rRNA gene indicated 98% similarity with the genus *Chromobacterium*. Partial 16SrRNA gene (GenBank accession number: FJ982784) of *Chromobacterium* sp. NIIST-CKK-01 was sequenced and aligned with other violacein producing strain's sequences in GenBank. The neighbor joining phylogenetic tree based on the 16SrRNA gene sequence showed that strain *Chromobacterium* sp. NIIST-CKK-01 fell within the radiation of cluster comprising *Chromobacterium*, *Janthinobacterium*, *Pseudoalteromonas* and *Duganella* (FIG. 1). The highest sequence similarity values were observed between *Chromobacterium* sp. NIIST-CKK-01 and its nearest neighbours in phylogenetic tree, namely *Chromobacterium* sp. 60 (EF077669), *Chromobacterium* sp. USM2 (FJ668944), *Chromobacterium* sp. MBIC 3901 (AB017487), *Chromobacterium piscinae* (AJ871127), etc. *Chromobacterium subtsugae* PRAA4 (AY 344056) covered in the U.S. Pat. No. 7,244,607 formed a separate Glade along with *Chromobacterium violaceum* (ATCC 12472, GenBank-M22510) and *Chromobacterium violaceum* CV09 (FJ 753567) FIG. 2. The phenotypic, genotypic and phylogenetic characteristics of *Chromobacterium* sp. NIIST-CKK-01 are different from *Chromobacterium subtsugae* PRAA4. Moreover, the bioactive pigment produced by *Chromobacterium* sp. NIIST-CKK-01 is stable over a wide temperature and pH.

EXAMPLES

The following examples are given by way of illustration and therefore should not be construed to limit the scope of the present invention.

Example 1

Production and Extraction of the Bioactive Pigment from the Culture of *Chromobacterium* sp. NIIST-CKK-01

Figure 2:
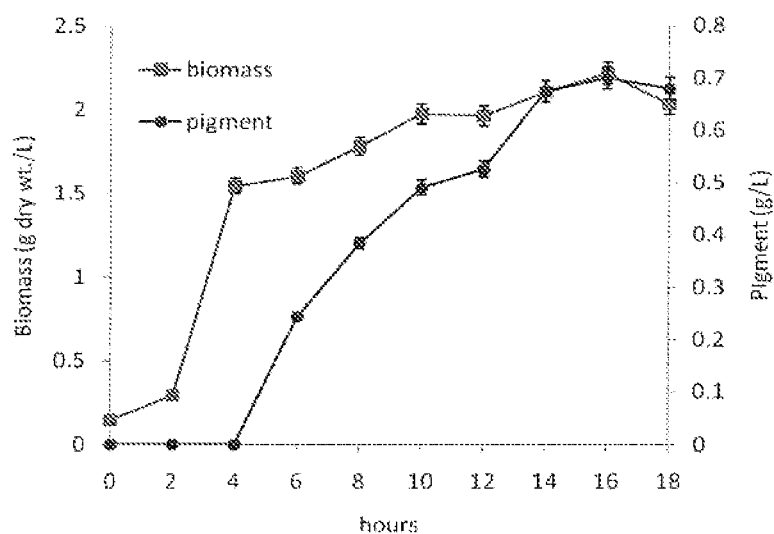
FIG. 2 shows biomass growth and pigment production profile of *Chromobacterium* sp. NIIST-CKK-01 in Luria Bertani (LB) broth at pH 7, and 30° C. under agitated (200 rpm) condition.

A loopful of 24 hrs old pure culture *Chromobacterium* sp. NIIST-CKK-01 from solid agar medium (LB agar or Nutrient agar) was inoculated with 50 ml of the growth medium (0.5% Yeast extract and 1.5% Peptone) taken in a 250 ml Erlenmeyer flask. Alternatively, 10% (v/v) of 24 hour old pure culture of *Chromobacterium* sp. NIIST-CKK-01 in LB broth was also used as inoculum. The pH of the medium was 7. The flasks inoculated with *Chromobacterium* sp. NIIST-CKK-01 were subsequently incubated in a rotary shaker at ambient temperature (30° C.) and 200 rpm for 24 hours. The deep purple purple-blue pigment starts appearing in the medium by about 6 hours of incubation and continued beyond biomass increase (FIG. 2).

After 24 hrs of incubation, the bacterial biomass with pigment was centrifuged at 9676.8×g and 4° C. for 10 minutes. After centrifugation, the clear supernatant was removed. The pellet containing biomass and pigment was mixed thoroughly with 5 ml of extra pure methanol. The mixture was centrifuged again at 9676.8×g and 4° C. for 10 minutes to separate the cell pellet from the solvent-pigment mixture. The pigment extraction was repeated twice using fresh solvent as described. All the pigment extracted solvent pooled together and the pigment was concentrated by normal vacuum drying in a desiccator. The quantity of biomass and pigment produced could be accounted by measuring optical density at 600 nm and 575 nm respectively. The yield of pigment by this method was about 1.0 g pigment/g of dry biomass in 24 hrs.

Figure 3:
FIG. 3 shows HPLC chromatogram of bioactive pigment in ethanolic solution performed on an ODS column with a mobile phase methanol and detector wavelength 575 nm (solvent flow rate 1 ml/min).
Figure 4:
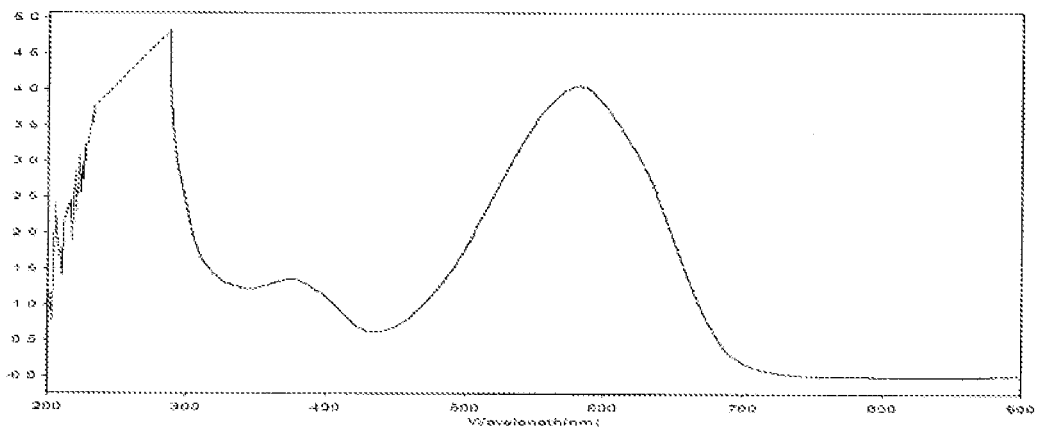
FIG. 4 shows UV-VIS Absorption spectrum of the violet pigment
Figure 5:
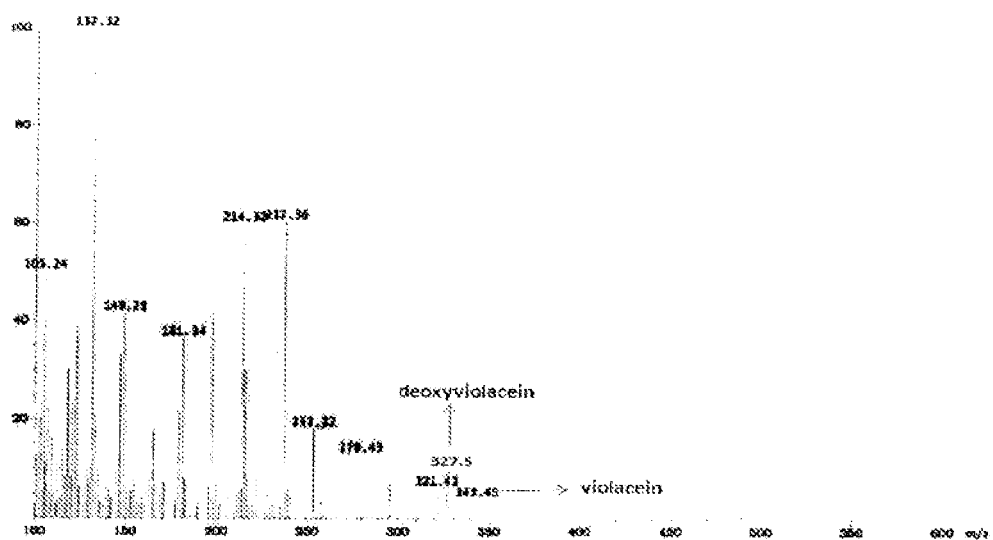
FIG. 5 shows Mass spectra of the crude pigment showing the presence of Violacein and deoxyviolacein in the pigment.

HPLC analysis is carried out for checking the purity of the pigment produced using an ODS column (LICHROSPHER-100; Merck) with acetonitrile (40%) at 1 ml/min as mobile phase and using UV-VIS detector at 575 nm (FIG. 3). UV-VIS absorption spectra indicated maximum absorption at 575 nm, typical of violacein and its derivatives (FIG. 4).

Example 2

Separation of the Bioactive Pigment from the Culture Medium of *Chromobacterium* sp. NIIST-CKK-01 Through Whole Broth Extraction As described in example 1, the violacein containing bioactive pigment was produced using pure culture of *Chromobacterium* sp. NIIST-CKK-01. After 24 hrs incubation, the entire broth (including biomass and pigment) was transferred to a 250 ml capacity separating flask. 10 ml of extrapure n-butanol was directly added to the broth in the separating flask and mixed thoroughly. The bioactive pigment dissolves in n-butanol and forms a separate layer at the top. The bottom layer containing mainly cell debris and traces of pigment was separated. The separated bottom portion was re-extracted again with 10 ml of n-butanol to recover the traces of pigment. The pigment containing n-butanol was pooled together and concentrated through drying in a rota vapour at 70° C.

Example 3

Production and Extraction of the Bioactive Pigment from the Culture of *Chromobacterium* sp. NIIST-CKK-01 Incubated at 25° C.

A loopful of 24 hrs old pure culture *Chromobacterium* sp. NIIST-CKK-01 from solid agar medium (LB agar) was inoculated with 50 ml of the growth medium (0.5% Yeast extract and 1.5% Peptone) taken in a 250 ml Erlenmeyer flask. Alternatively, 10% (v/v) of 24 hour old pure culture of *Chromobacterium* sp. NIIST-CKK-01 in LB broth or Nutrient broth medium was also used as inoculum. The pH of the medium was 7. The flasks inoculated with *Chromobacterium* sp. NIIST-CKK-01 was subsequently incubated in a rotary shaker at 25° C. temperature and 200 rpm for 24 hours. The deep purple purple-blue pigment starts appearing in the medium by about 12 hours of incubation and continued beyond biomass increase.

After 24 hrs of incubation, the liquid culture medium containing the pigment and biomass was transferred to a 250 ml capacity separating flask. 10 ml of extrapure n-butanol was directly added to the broth in the separating flask and mixed thoroughly. The bioactive pigment dissolves in n-butanol and forms a separate layer at the top. The bottom layer containing mainly cell debris and traces of pigment was separated. The separated bottom portion was re-extracted again with 10 ml n-butanol to recover the trace of pigment. The pigment containing n-butanol was pooled together and concentrated through drying in a rotavapour at 70° C. The yield of pigment by this method was about 0.7 g pigment/g of dry biomass in 24 hrs.

Example 4

Production and Extraction of the Bioactive Pigment from the Culture of *Chromobacterium* sp. NIIST-CKK-01 Incubated at 35° C.

A loopful of 24 hrs old pure culture *Chromobacterium* sp. NIIST-CKK-01 from solid agar medium (LB agar) was inoculated with 50 ml of the growth medium (0.5% Yeast extract and 1.5% Peptone) taken in a 250 ml Erlenmeyer flask. Alternatively, 10% (v/v) of 24 hour old pure culture of *Chromobacterium* sp. NIIST-CKK-01 in LB broth or Nutrient broth medium was also used as inoculum. The pH of the medium was in the range of 7. The flasks inoculated with *Chromobacterium* sp. NIIST-CKK-01 was subsequently incubated in a rotary shaker at 35° C. temperature and 200 rpm for 24 hours. The deep purple purple-blue pigment starts appearing in the medium by about 12 hours of incubation and continued beyond biomass increase.

After 24-30 hrs of incubation, the liquid culture medium containing the pigment and biomass was transferred to a 250 ml capacity separating flask. 10 ml of extrapure n-butanol was directly added to the broth in the separating flask and mixed thoroughly. The bioactive pigment dissolves in n-butanol and forms a separate layer at the top. The bottom layer containing mainly cell debris and traces of pigment was separated. The separated bottom portion was re-extracted again with 10 ml n-butanol to recover the trace of pigment. The pigment containing n-butanol was pooled together and concentrated through drying in a rotavapour at 70° C. The yield of pigment by this method was about 0.6 g pigment/g of dry biomass in 24 hrs.

Example 4

Figure 6:
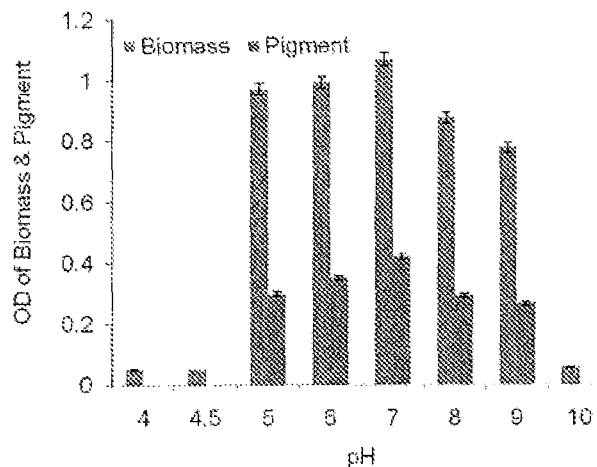
FIG. 6 shows the effect of different pH on biomass growth and pigment production by *Chromobacterium* NIIST-CKK-01. Optical Density (OD) value measured after 24 hrs of incubation under specific pH of growth media is shown. OD of biomass and pigment were measured at 600 and 575 nm respectively.

Production of the Bioactive Pigment from the Culture of *Chromobacterium* sp. NIIST-CKK-01 Incubated at Different pH The response of media pH on violacein production was studied in batch experiments. The pH of the medium (0.5% Yeast extract and 1.5% Peptone) was initially adjusted to 4,5,6,7,8, 9 and 10 separately by adding acid or alkali. Media at each pH was inoculated with loopful of 24 hrs old pure culture of *Chromobacterium* sp. NIIST-CKK-01. The effect of pH on growth and pigment production in *Chromobacterium* sp. NIIST-CKK-01 is shown in FIG. 6. Growth and pigment production by the strain was observed over a pH range of 5-9, with optimum growth observed at pH around 7.

At pH 4 and pH 10 slight bacterial growth was observed, but there was no pigment production.

Example 5

Figure 7:
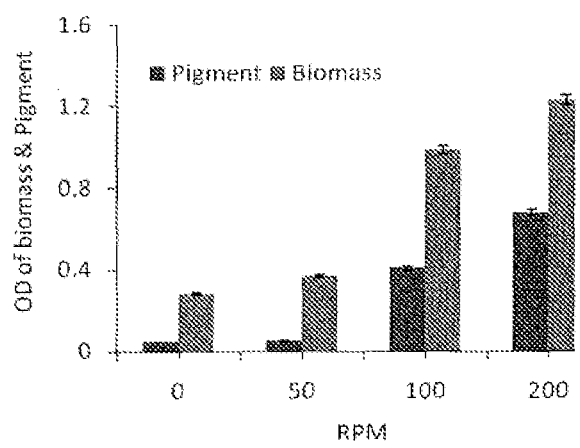
FIG. 7 shows the effect of agitation at different rpm on growth and pigment production by *Chromobacterium* NIIST-CKK-01. OD value measured after 24 hrs of incubation under specific RPM is shown. OD of biomass and pigment were measured at 600 and 575 nm respectively.

Production of the Bioactive Pigment from the Culture of Chromobacterium sp. NIIST-CKK-01 Incubated at Different Agitation Speed The response of media agitation on violacein production was studied in batch cultures. Growth medium (0.5% Yeast extract and 1.5% Peptone) at neutral pH (pH 7) was inoculated with loopful of 24 hrs old pure culture Chromobacterium sp. NIIST-CKK-01 and incubated in a rotary shaker set at different agitation speeds or RPM (revolutions per minute). Response of the isolate on growth and pigment production under different agitation speeds is shown in FIG. 7. Both static and agitated cultures exhibited growth as well as pigment production. There was significant increase in biomass and pigment production at higher agitations.

Example 6

Characteristics of the Bioactive Pigment Extracted from Chromobacterium sp Having Accession No. MTCC 5522

Light Sensitivity of the Bioactive Pigment

The extracted bioactive pigment containing violacein and its derivatives decolourised when kept under direct sunlight. This indicates that the violacein pigment decomposed and was therefore not stable under direct sunlight whereas the pigment remained stable in dark for 2 weeks.

Thermo-Stability and pH Stability of the Bioactive Pigment

The pigment remained stable at a temperature of 80° C. for 1 hour and at the storage temperature of 4° C. for the tested period of 2 weeks (Table 1). The pigment was stable at pH range of 2-8 for 2 weeks of incubation in dark (Table 2)

Antibacterial Activity of the Bioactive Pigment from Chromobacterium sp. NIIST-CKK-01

Figure 8A:
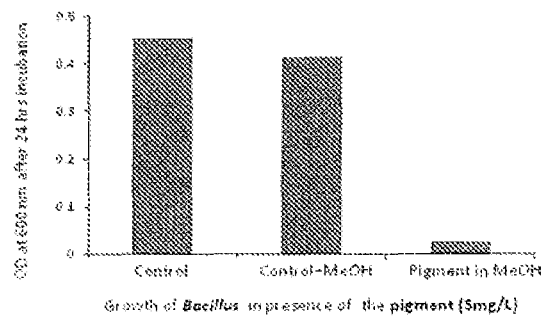
FIG. 8a and 8b shows the antimicrobial activity of crude pigment at concentration 5 mg/L on gram-positive (*Bacillus*) in FIG. 8a and gram-negative (*Pseudomonas*) bacteria in FIG. 8b. Growth of bacteria is represented by OD reading at 600 nm. Control+methanol (MeOH) were put up to account the inhibitory effect of methanol (MeOH) on growth.
Figure 8B:
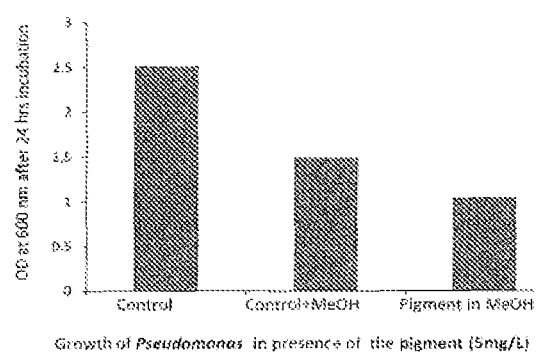

The extracted violacein and its derivatives containing bioactive pigment exhibited 93-97% inhibition of antibacterial activity against gram-positive bacteria, Bacillus (FIG. 8a). For gram-negative bacteria, Pseudomonas the inhibition was around 55-60% (FIG. 8b).

Antifungal Activity of the Bioactive Pigment from Chromobacterium sp. NIIST-CKK-01

The extracted violacein and its derivatives containing bioactive pigment exhibited 10-15% inhibition of growth in Penicillium. The experiment was carried out using pigment at concentration 5 mg/L which was initially dissolved in ethanol and added to the fungal culture. A control was performed with the same volume of ethanol alone used to dissolve the pigment. The incubation temperature and pH were 30° C. and 7 respectively. After 48 hours of incubation, the dry weight of fungal biomass was quantified. Around 10-20% decline in fungal biomass was observed in the bioactive pigment added culture.

Antiprotozoal Activity of the Bioactive Pigment from Chromobacterium sp. Having Accession No. MTCC 5522(NIIST-CKK-01)

The extracted violacein and its derivatives containing bioactive pigment exhibited 20 to 30% inhibition of Ciliate protozoa growth.

Antioxidant Activity of the Bioactive Pigment from Chromobacterium sp. Having Accession No. MTCC 5522

Free-radical scavenging potentials of the pigment was tested against a methanolic solution of 2, 2 Diphenyl 1-1 Picryl Hydrazyl (DPPH). The pigment was incubated in methanolic solution of DPPH (0.1 mM) for 20 minutes and optical density measured at 517 nm. A control was performed in parallel with 100% DPPH in the absence of the pigment. Gallic acid (1 mg/ml stock) in methanol was used as a standard. The crude violet pigment showed a maximum of 64% antioxidant activity against DPPH, and the antioxidant potential was obtained as IC 50 (inhibitory concentration) of 0.6 mg/ml.

ADVANTAGES OF THE INVENTION

1. Higher production of violacein and its derivatives containing bioactive pigment.
2. Pigment production in short duration of time.
3. Simple growth requirements for maintaining and growing the bacterium producing the bioactive pigment.
4. L-Tryptophan, the precursor for violacein synthesis is not required in the growth medium.
5. Simple separation and purification of the bioactive pigment produced through whole broth extraction.

I claim:

1. A process for producing a microbial purple-blue bioactive pigment containing violacein and its derivative deoxyviolacein using Chromobacterium sp. MTCC 5522, wherein the Chromobacterium cells are 0.3 to 0.6 µm wide and 0.9 to 1.5 µm long, facultative aerobic Gram negative, oxidase positive, indole production test negative, methyl red test positive, Voges-Proskauer test negative, citrate utilization test positive, TSI test glucose fermenting only, catalase test negative and ureas test negative, the process comprising:
   (a) inoculating Chromobacterium sp. MTCC 5522 in a growth medium at a pH in the range of 5 to 9 at a temperature in the range of 27 to 32° C. for a time period in the range of 8 to 30 hrs under stirring at 150 to 250 rpm to obtain a bacterial biomass containing pigment;
   (b) mixing the bacterial biomass containing pigment as obtained in step (a) with a solvent in the ratio ranging between 1:3 to 1:5 to obtain a mixture;
   (c) centrifuging the mixture as obtained in step (b) at a speed in the range of 9660×g to 10,000×g at a temperature ranging between 4° C. and 7° C. for a period in the range of 10 to 15 minutes to obtain a solvent extracted pigment;
   (d) concentrating the solvent extracted pigment as obtained in step (c) by rotary evaporation or vacuum drying at a temperature ranging between 50° C. to 70° C. to obtain the microbial purple-blue bioactive pigment containing violacein and its derivative deoxyviolacein.

2. A process as claimed in of claim 1, wherein in step (a), the pH is in the range of 6.5 to 7.5 and the time period is in the range of 20 to 24 hrs.

3. A process as claimed in claim 1, wherein the growth medium in step (a) comprises either:
   (i) 0.4 to 0.5% yeast extract and 1 to 1.5% peptone; or
   (ii) 0.5 to 1% starch, 0.25 to 0.75% peptone, and 0.1 to 0.3% yeast extract.

4. A process as claimed in claim 1, wherein the solvent used in step (b) is selected from the group consisting of ethanol, methanol, butanol and a combination thereof.

5. A process as claimed in claim 1, wherein the time period of step (a) is 24 hrs.

6. A process for producing a microbial purple-blue bioactive pigment containing violacein and its derivative deoxyviolacein using Chromobacterium sp. MTCC 5522, wherein the *Chromobacterium* cells are 0.3 to 0.6 μm wide and 0.9 to 1.5 μm long, facultative aerobic Gram negative, oxidase positive, indole production test negative, methyl red test positive, Voges-Proskauer test negative, citrate utilization test positive, TSI test glucose fermenting only, catalase test negative and ureas test negative, the process comprising:

(a) inoculating *Chromobacterium* sp. MTCC 5522 in a growth medium at a pH in the range of 5 to 9 at a temperature in the range of 27 to 32° C. for a time period in the range of 8 to 30 hrs under stirring at 150 to 250 rpm to obtain a bacterial biomass containing pigment;

(b) centrifuging the bacterial biomass containing pigment as obtained in step (a) at a speed in the range of 9660×g to 10000×g at a temperature ranging between 4 to 7° C. for a time period in the range of 10 to 15 minutes to obtain a cell pellet containing the bacterial biomass and pigment;

(c) mixing the cell pellet containing the bacterial biomass and pigment as obtained in step (b) with a solvent in the ratio ranging between 1:3 and 1:5 to obtain a mixture;

(d) centrifuging the mixture as obtained in step (b) at a speed in the range of 9660×g to 10000×g at a temperature ranging between 4 to 7° C. for a time period in the range of 10 to 15 minutes to obtain a solvent extracted pigment;

(e) concentrating the solvent extracted pigment as obtained in step (d) by rotary evaporation or vacuum drying at a temperature ranging between 50° C. and 70° C. to obtain the microbial purple-blue bioactive pigment containing violacein and its derivative deoxyviolacein.

* * * * *